United States Patent
Balzano

(10) Patent No.: US 7,186,249 B1
(45) Date of Patent: Mar. 6, 2007

(54) THERMALLY CONDUCTIVE SURGICAL PROBE

(76) Inventor: Alfiero Balzano, 11371 Monarch St., Garden Grove, CA (US) 92841

( * ) Notice: Subject to any disclaimer, the term of this patent is extended or adjusted under 35 U.S.C. 154(b) by 131 days.

(21) Appl. No.: 10/754,138

(22) Filed: Jan. 9, 2004

Related U.S. Application Data

(60) Provisional application No. 60/440,098, filed on Jan. 16, 2003.

(51) Int. Cl.
*A61B 18/18* (2006.01)

(52) U.S. Cl. ................................... 606/27

(58) Field of Classification Search ........... 606/20–26, 606/27–34; 361/386
See application file for complete search history.

(56) References Cited

U.S. PATENT DOCUMENTS

| | | | | |
|---|---|---|---|---|
| 5,224,030 | A * | 6/1993 | Banks et al. | 361/717 |
| 5,609,562 | A * | 3/1997 | Kaali | 600/114 |
| 5,676,681 | A * | 10/1997 | Yoon | 606/185 |
| 5,814,058 | A * | 9/1998 | Carlson et al. | 606/185 |
| 5,906,612 | A * | 5/1999 | Chinn | 606/20 |
| 6,302,898 | B1 * | 10/2001 | Edwards et al. | 606/214 |

* cited by examiner

*Primary Examiner*—Roy D. Gibson
*Assistant Examiner*—Pete Vrettakos
(74) *Attorney, Agent, or Firm*—Stetina Brunda Garred & Brucker

(57) ABSTRACT

A surgical apparatus and process for freezing or cauterizing a particular infected body area employing a transparent sleeve insertable through a small slit in the flesh of a patient and wherein the inserted end of the sleeve is provided with a cone-shaped tip having a plurality of segments normally self biased to close to define a dull pointed end susceptible for expansion when a solid, rigid probe is inserted through the sleeve. The end of the probe includes a conical or cone-shaped tip with a small extension or projection that causes expansion of the flaps on the tip of the sleeve. The extension on the end of the probe is placed in alignment position to locate the infected organ or area to be removed. Monitoring of the sleeve and probe insertion and location of the infected area is achieved by video camera. After removing the solid and rigid probe, a fiber optic tube is inserted into the sleeve whereby ambient light is conducted through the tube to the advancing end of the sleeve. A carbon rod is inserted through the fiber optic tube so as to have its pointed end in contact with the tumor, body organ or infected area. The carbon rod is connected to a source of cold or heat. In a cold application, the infected area or tumor is frozen so that when the carbon rod is removed and replaced by a suction device, the frozen infected area or tumor can be fragmented and the particles removed.

6 Claims, 1 Drawing Sheet

THERMALLY CONDUCTIVE SURGICAL PROBE

Priority claimed based on Ser. No. 60/440,098 filed Jan. 16, 2003 pending.

BACKGROUND OF THE INVENTION

1. Field of the Invention

The present invention relates to the field of medical devices and more particularly to a novel surgical probe and process for medical use, whereby a thermal conductive probe is introduced to a diseased or tumor affected area of the body, whereby the infection or tumor is solidified sufficiently so that subsequent removal of hardened particles, cells or the like can be withdrawn by suction means.

2. Brief Description of the Prior Art

In the past, it has been a typical practice in the medical field to remove a tumor by employing surgical methods which require extensive invasive procedures and which cause considerable discomfort, pain, and protracted healing time. Therefore, a long-standing need has existed to provide a surgical device and method which would readily define, identify, and provide a safe, disposable probe solution whereby medical doctors may insert, position, contact and terminate an undesirable internal area or organ inclusive of removal thereof and eliminating or minimizing the spread of associated infectious cells. Such a surgical probe solution must employ the smallest possible entry requirement, so as to minimize trauma and escalate the patient's recovery.

A long-standing need has existed to provide a surgical instrument such as a thermal conductive probe which enters a small slit in the skin area, whereby the thermal conductive probe can be inserted and placed adjacent to an infected organ or area. The thermal conductive probe must be able handle and conduct extremely cold or hot temperatures proficient to freeze and/or cauterize the undesired internal organ or area.

SUMMARY OF THE INVENTION

Accordingly, the above problems and difficulties are avoided by the present invention which provides a novel, surgical apparatus and process for freezing or cauterizing a particular infected body area that employs a transparent sleeve which is inserted through a small slit in the flesh of a patient and wherein the inserted end of the sleeve is provided with a cone-shaped tip having a plurality of segments normally self biased to close to define a dull pointed end susceptible for expansion when a solid, rigid probe is inserted through the sleeve. The end of the probe includes a conical or cone-shaped tip with a small extension projection that causes expansion of the flaps on the tip of the sleeve. The extension on the end of the probe is positioned to locate the infected body organ or area to be operated upon. With the assistance of a location observation device, such as a video camera, observation and monitoring of the insertion procedure and precise location of the infected area is achieved followed by removing the solid and rigid probe and subsequent insertion into the sleeve of a fiber optic tube. Ambient light is conducted through the tube to the advancing end of the sleeve. A video camera is then inserted into the optical tube and visual images are presented to the surgical staff on a monitor or video display. Once the infected area has been located and the end of the sleeve placed adjacent thereto, the video camera is removed from the bore of the fiber optic tube and a carbon rod is inserted through the fiber optic tube, so as to have its pointed end partially extending through the flaps of the conical end of the sleeve. The latter end is in contact with the tumor, body organ or infected area intended to be removed. The carbon rod is connected to a source of cold, such as controlled liquid nitrogen, Freon or if heat is required, connected to a finitely controlled electrical heat source. In the instance of cold application, the infected area or body organ or tumor is substantially frozen so that when the carbon rod is removed and replaced by a suction device, the frozen infected area, body organ or tumor can be broken down into fragments and the particles, including the infected cells, removed. Once collected, the particles can be disposed in a safe and non-injurious manner. The frozen body organ or tumor will contain its frozen cells within the initial tissue sleeving, which surrounds the area, such that infected cells are precluded from spreading to other areas.

Therefore, it is among the primary objects of the present invention to provide a surgically thermal conductive probe which is useful in a surgical procedure to define, identify, and provide a safe, disposable means that doctors can use to insert, position, contact and terminate, by freezing or cauterizing, an undesired internal area or body organ.

Another object of the present invention is to provide a surgical thermal conductive probe which not only will provide the above solution but also includes means for removal of frozen or cauterized infected areas, eliminating or minimizing the spread of associated infected or undesirable cells.

Still another object of the present invention is to provide a surgical procedure and thermally conductive probe which can be inserted through the smallest possible entry in the skin and which can be removed through the entry, allowing for a minimum recovery time, in comparison to present day methods.

Yet another object resides in providing a thermally conductive probe for surgical purposes which is sufficient to conduct extreme cold or heat at an extremely high rate, such as up to five times that of copper, and which would, after being positioned after insertion into the body, maneuvered so as to contact the exact area to be treated.

Still a further object resides in providing a thermal composite material for a surgical probe, whereby a surgeon can activate thermal conductivity of an extreme nature to the area of infection, tumor or body organ, while restricting the movement of the probe and precluding infected cells from spreading to other body areas.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

DESCRIPTION OF PREFERRED EMBODIMENT

Figure 1:
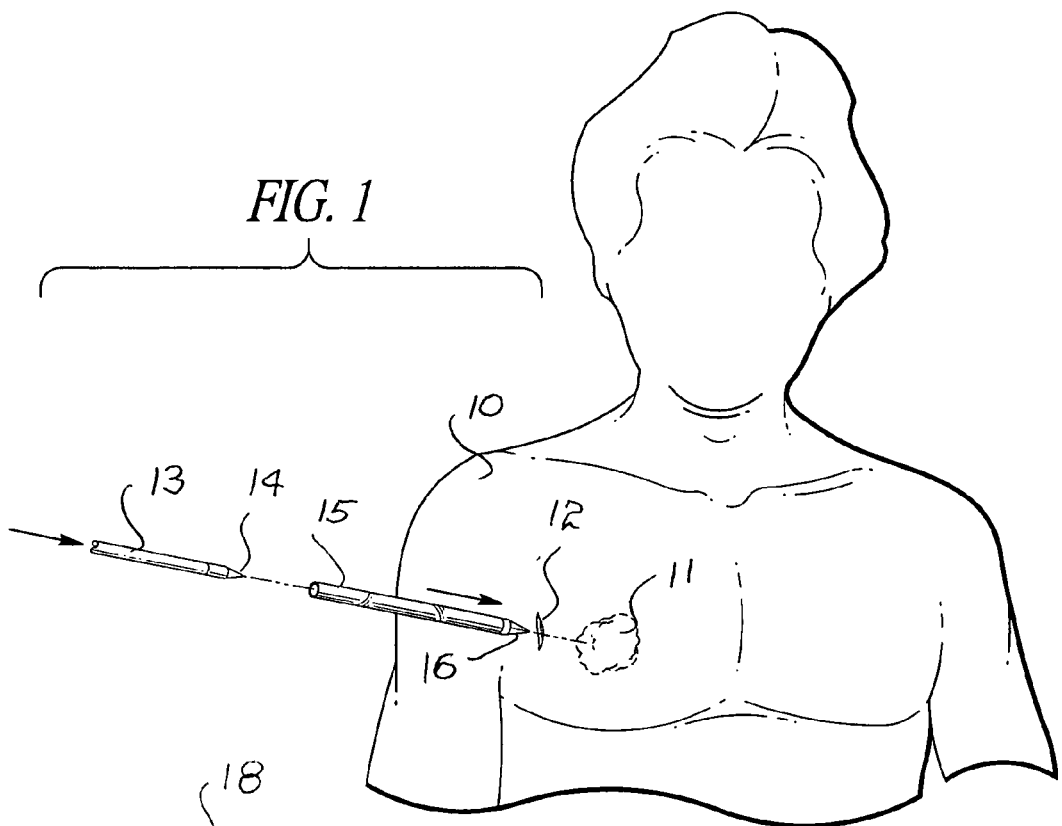
FIG. 1 is a diagrammatic perspective view illustrating insertion of the thermally conductive probe apparatus through a small insertion in the skin and flesh of a patient.

Referring now to FIG. 1, a patient is indicated by the numeral 10 having an infected area or tumor 11 which requires surgery for achieving removal. In accordance with use of the present invention, a slight incision is made in the vicinity of the area 11, and the incision is indicated by numeral 12. A steel rod 13 having a pointed or conical end 14 is inserted through the open end of a sleeve 15 and advanced through the sleeve 15 so that the conical end 14 terminates within a flapped conical end 16 of the sleeve. Subsequently, the sleeve and the rod 13 are inserted simultaneously through the incision and advanced through surrounding tissue in the direction of the infected area or tumor 11.

Figure 2:
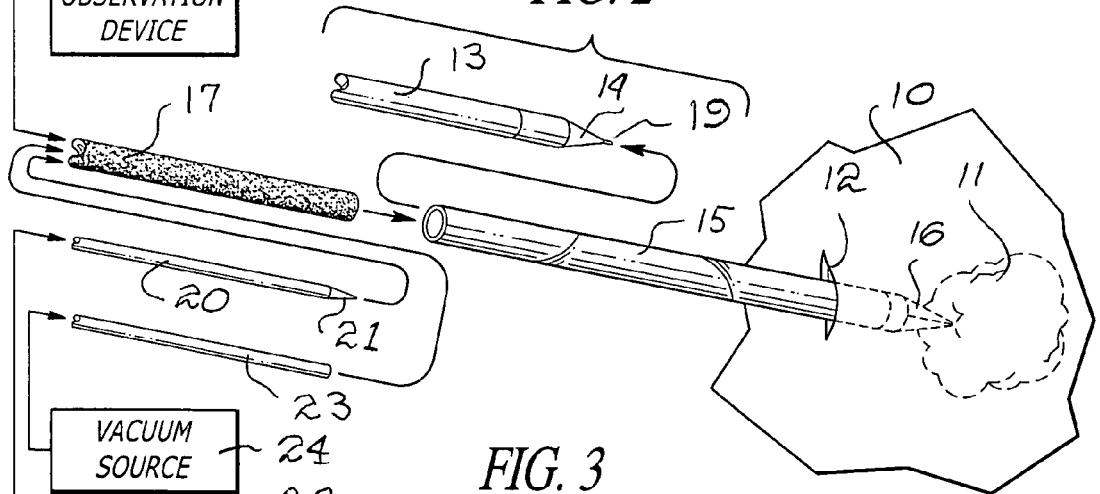
FIG. 2 is an enlarged, exploded perspective view of the thermally conductive probe apparatus and system employed in the performance of a tissue removal procedure.

Referring to FIG. 2, it can be seen that the rod within sleeve 15 is advanced until an extension 19 at the tip of the rod is immediately adjacent to the infected area or tumor 11. At this time when the area to be worked upon is located, the rod 13 is removed from the sleeve 15 and replaced with a fiber optic tube 17, so that the end of the tube 17 terminates immediately adjacent to the end of sleeve 15 and adjacent to the flapped end 16. Ambient light is carried through the tube 17 to illuminate the body area ahead of the sleeve 15. Next, a miniature or micro-camera is introduced into the base of the optical tube 17 and such a camera is indicated by numeral 18 which serves as a location observation device. The viewing device or camera may be inserted at the exposed end of the fiber optic tube 17 or may be coupled to a light source so that an internal light in the device can be emitted adjacent to the infected area or tumor 11. Thereby the surgeon in positioning the end of the sleeve 15 can properly locate the terminating flap end 16 adjacent to the area or tumor. The camera or observation device will provide a visual assistance in locating the infected area or tumor by means of a remotely located television display or a monitor display. Upon locating the infected or tumor area, the location observation device 18 is removed as well as the fiber optic tube 17. These latter elements are replaced by a carbon rod 20 having a conical end or tip 21 which is inserted into the previously inserted tube 15 until the conical end mates with the flap end 16 of the sleeve. With slight pressure, the flap end of the sleeve expands to permit the tip of the carbon rod 20, as indicated by numeral 21, to actually touch the infected area or tumor 11. It is to be noted that the opposite end of the rod from the tip 21 is connected to a source of cold, such as Freon or finitely controlled liquid nitrogen 22.

In other surgical procedures, the source of cold 22 is replaced with a finitely controlled electrical heating source when such surgical operations are warranted.

Once positioned, the carbon rod 20, made of a thermal graphite composite, such as described in U.S. Pat. No. 6,257,329, is inserted in the fiber optic tube until the end or tip 21 reaches the infected area or tumor 11. The source of cold is activated and the extremely low temperature is conducted via the carbon rod 20 to the infected area or tumor 11. The consequence is that the infected area or tumor is frozen and/or cauterized. The thermal composite carbon rod 20 is able to conduct extreme cold (or heat) at an extremely high rate, such as up to five times that of copper. The surgeon may now activate the thermal conductivity of an extreme nature to the area of concern which "terminates" any living cells while restricting cellular movement while containing the frozen, terminated cells in their same tissue sleeving, precluding infected cells from spreading to other surrounding areas. Next, the thermal conductive composite rod is removed from the tube 15 and the optical tube 17 now allows for insertion of an organ or tissue removing element, such as a suction tube 23. By activating a vacuum source 24 and using the organ or tissue removing element 23, inclusive of vacuum assist, removal of the terminated tissues and associated cells completes the procedure. When the entire surgical procedure is completed, the sleeve 15 is removed from the initial incision 12 and, thus, allows for a minimum recovery time, in comparison to other conventional surgical methods.

Figure 3:
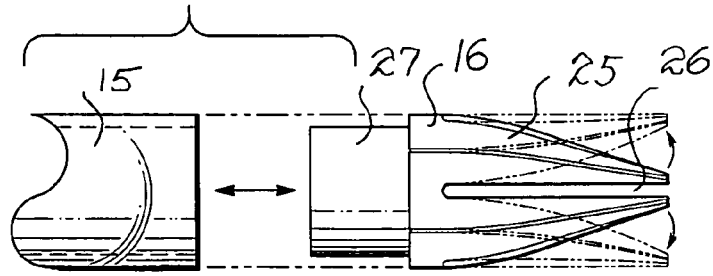
FIG. 3 is an enlarged side-elevational view of the end of the sleeve illustrating the conical, segmented end thereof.

Referring now to FIG. 3, it can be seen that the end of transparent tube 15 is provided with the conical element 16, wherein a plurality of flaps or segments, such as segment 25, are separated by slots, such as slot 26, so that when the conical tip 14 on probe 13 or the carbon rod 20 is introduced through the bore of the sleeve 15, the conical tip will enter the conical element 16 causing the segments to deploy outwardly in the direction of the arrows illustrated, which permits the tip 17 on rod 13 to touch or engage the infected area or tumor 11, or in the case of the carbon rod 20, the conical tip 21 will open the flaps on the flap element 16 to touch the infected area or tumor. The flap conical element 16 includes a collar or base 27 that is inserted into the end of the sleeve 15 for removable attachment therewith. Such attachment is shown by the double arrows indicating that the tip may be installed on the end of the sleeve or removed therefrom.

Therefore, it can be seen that the objective of the present invention is to define, identify and provide for a safe disposable surgical solution that medical doctors can use to insert, position, contact and terminate such as by freezing and/or cauterizing an undesirable internal area or organ, inclusive of removing of the area or organ, eliminating or minimizing the spread of associated undesirable cells. The hardware solution meets the smallest possible entry requirement, so as to minimize trauma and escalate the patient's recovery.

Initially, the plastic sleeve 15 is inserted through an incision and is electrically insulated and takes the form of the transparent sleeve 15. Approximately ⅜" outer diameter and a ¼" inner diameter is employed, inclusive of a segmented, movable "butterfly" tip, constituting the flapped conical element 16 on one end and an open diameter on the other end. An additional solid rod or probe composed of surgical plastic or stainless steel matching the approximate inner diameter of the sleeve bore is installed in the bore and is used to maintain the insulated tube diameter during processing and handling, so as to prevent flexing or distortion. Prior to or shortly after insertion into the infected surgical area, the stainless steel or surgical plastic rod is removed followed by introducing the fiber optic sleeve or tube 17 into the bore of the sleeve 15. The fiber optic sleeve or tube has an outside diameter matching the inside diameter of the sleeve 15, but having an even smaller inside diameter, such as ⅛" tube or ¹⁄₁₆th of an inch, permitting the insertion of a light and video camera. The operating surgeon has access to the visual deployment of the sleeve within the incision 12 by access to visibility from the viewing end the light tube and by means of the location observation device including a monitor or TV display.

Once the sleeve 15 has been positioned, the thermal graphite composite or carbon rod 20 is inserted in the inside diameter of the fiber optic plastic tube 17. The thermal composition of the carbon rod being able to conduct extremely cold or heat at an extremely high rate, such as up to five time that of copper, would, after being positioned and slid forward so as to contact the area being treated, conduct the source of heat or cold directly to the affected area. The source for cold being finitely controlled liquid nitrogen and/or a finitely controlled electrical heat source.

The surgeon can now actuate thermal conductivity of an extreme nature to the area of the infected area so as to terminate by freezing or heating the infected cells or tumor, while restricting its movement and containing the frozen particles in its original tissue sleeving so as to preclude infected cells from spreading to other areas. When frozen, the cells are extremely hard and have a tendency to fragment into smaller particles so that they can be removed by suction when the thermal composite rod is withdrawn and a suction tube or element is introduced into the sleeve 15.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A thermal conductive surgical probe assembly for freezing or cauterizing an infected area, damaged tissue, or tissue growth in a body structure comprising:
    an elongated transparent sleeve having a first end and a second end, said transparent sleeve including a conical element disposed on said second end and having a plurality of flaps separated by slots and adapted to be deployed outwardly in response to insertion of said location probe or said thermal rod, said conical element operative to surround the infected area, damaged tissue, or tissue growth;
    a location probe removably insertable through said sleeve and having a distal end projecting beyond said second end of said sleeve;
    a fiber optical tube carried in said sleeve in the absence of said location probe; and
    a thermal conductive rod insertable into said optical tube having a conical tip projecting ahead of said sleeve second end and said optical tube for applying thermal energy to the infected area, damaged tissue, or tissue growth, said thermal rod being composed of a graphite carbon composition having a thermal conductivity rate of five times the conductivity rate of copper.

2. The thermal conductive surgical probe assembly defined in claim 1 wherein:
    said location probe includes an extension carried on said distal end projecting externally of said conical element through said plurality of flaps.

3. The thermal conductive surgical probe assembly defined in claim 1 including:
    a miniature camera insertable into and through said fiber optical tube preparatory for insertion of said thermal conductive rod.

4. The thermal conductive surgical probe assembly defined in claim 3 including:
    a monitoring display coupled to said camera.

5. The thermal conductive surgical probe assembly defined in claim 1 including:
    a cold source operably coupled to said thermal conductive rod for applying a low temperature causing the infected area, damaged tissue or tissue growth to fragment into micro-particles.

6. The thermal conductive surgical probe assembly defined in claim 5 including:
    a vacuum device insertable through said tube in the absence of said thermal conductive rod for removal of fragmented particles.

* * * * *